United States Patent
Kota et al.

(10) Patent No.: US 12,314,656 B1
(45) Date of Patent: May 27, 2025

(54) SYSTEMS AND METHODS TO BRIEFLY DEVIATE FROM AND RESUME BACK TO AMENDING A SECTION OF A NOTE

(71) Applicant: Suki AI, Inc., Redwood City, CA (US)

(72) Inventors: Nithyanand Kota, Santa Clara, CA (US); Yashas Rao, San Francisco, CA (US); Hao Ran Raymond Lin, San Francisco, CA (US); Maneesh Dewan, Sunnyvale, CA (US); Arunan Rabindran, San Mateo, CA (US); Jatin Chhugani, Mountain View, CA (US); Sudheer Tumu, Santa Clara, CA (US)

(73) Assignee: Suki AI, Inc., Redwood City, CA (US)

( * ) Notice: Subject to any disclaimer, the term of this patent is extended or adjusted under 35 U.S.C. 154(b) by 0 days.

(21) Appl. No.: 18/606,824

(22) Filed: Mar. 15, 2024

Related U.S. Application Data (63) Continuation of application No. 18/300,120, filed on Apr. 13, 2023, now Pat. No. 11,934,769, which is a continuation of application No. 17/875,052, filed on Jul. 27, 2022, now Pat. No. 11,630,943, which is a
(Continued)

(51) Int. Cl.
| | |
|---|---|
| *G06F 17/00* | (2019.01) |
| *G06F 40/166* | (2020.01) |
| *G10L 15/07* | (2013.01) |
| *G10L 15/08* | (2006.01) |
| *G10L 15/22* | (2006.01) |

(Continued)

(52) U.S. Cl.
CPC ............ *G06F 40/166* (2020.01); *G10L 15/07* (2013.01); *G10L 15/083* (2013.01); *G10L 15/22* (2013.01); *G10L 15/26* (2013.01); *G16H 15/00* (2018.01); *G10L 2015/088* (2013.01)

(58) Field of Classification Search
CPC ... G10L 2015/088; G10L 15/26; G10L 15/22; G10L 15/083; G10L 15/07; G16H 15/00; G06F 40/166
See application file for complete search history.

(56) References Cited

U.S. PATENT DOCUMENTS

| | | | |
|---|---|---|---|
| 8,504,372 B2 * | 8/2013 | Carraux | G10L 15/22 704/270.1 |
| 8,930,210 B2 * | 1/2015 | Oez | G10L 15/26 705/2 |

(Continued)

*Primary Examiner* — Mohammed H Zuberi
(74) *Attorney, Agent, or Firm* — Esplin & Associates, PC (57) ABSTRACT

Systems and methods to briefly deviate from and resume back to amending a section of a note are disclosed. Exemplary implementations may: obtain audio information representing sound captured by an audio section of a client computing platform, such sound including speech from a user associated with the client computing platform; effectuate presentation of a graphical user interface that includes sections of the note; analyze the audio information to determine which individual ones of the spoken inputs are the primary spoken input or the deviant spoken input; determine, based on analysis, which section of the note to which the deviant spoken input is related; alternately amend, based on the determination, sections of the note by deviating from one section to another section and returning back to the one section for continued population; and effectuate, via the user interface, presentation of the alternating amendments to the sections of the note.

16 Claims, 5 Drawing Sheets

Related U.S. Application Data continuation of application No. 17/146,029, filed on Jan. 11, 2021, now Pat. No. 11,429,780.

(51) Int. Cl.
*G10L 15/26* (2006.01)
*G16H 15/00* (2018.01)

(56) References Cited

U.S. PATENT DOCUMENTS 10,586,466 B2 * 3/2020 Waterhouse ............. G09B 5/02
10,930,268 B2 * 2/2021 Yoo ......................... G06F 18/24

* cited by examiner

Patient Name            50

Section 1
Parameter 1: Value 1
Parameter 2: Value 2

Section 2
Description 2

FIG. 4

SYSTEMS AND METHODS TO BRIEFLY DEVIATE FROM AND RESUME BACK TO AMENDING A SECTION OF A NOTE

FIELD OF THE DISCLOSURE

The present disclosure relates to systems and methods to briefly deviate from and resume back to amending a section of a note.

BACKGROUND

Users (e.g., medical professionals, transcribers) may detail a plurality of information to be recorded in a document. The plurality of information may often categorize into various sections for organization of the document. The user may briefly digress from dictating an initial thought/information and dictate an unrelated thought/other information, and resume dictation of the initial thought. Subsequently, both the initial thought, in its entirety, and the unrelated thought should be appropriately categorized within the document.

SUMMARY

One aspect of the present disclosure relates to facilitating note editing. As the users dictate information that is the basis of an amendment in a particular part of the note, a system of the present disclosure may enable the user to deviate from dictation of the information for the particular part and dictate additional information. The additional information may be analyzed to determine where in the note the additional information is related. An additional amendment may be implemented based on the additional information. The user may subsequently resume to dictation of the information they were initially dictating and the amendment in accordance with the information for that part may resume. As such, the user is not required to manually indicate where amendments related to additionally dictated information (i.e., deviant from the initial information dictated) should occur and thus streamlining note editing to save time and promote efficiency.

One aspect of the present disclosure relates to a system configured to briefly deviate from and resume back to amending a section of a note. The system may include one or more hardware processors configured by machine-readable instructions. Machine-readable instructions may include one or more instruction components. The instruction components may include computer program components. The instruction components may include one or more of audio information component, presentation component, amendment component, and/or other instruction components.

The audio information component may be configured to obtain audio information representing sound captured by an audio section of a client computing platform. The sound may include speech from a user associated with the client computing platform. The client computing platform may include a user interface, the audio section, and/or other elements. The audio information may include spoken inputs uttered by the user. The spoken inputs may include primary spoken input, deviant spoken input, and/or other spoken inputs. Portions of the primary spoken input may be spoken temporally prior to and subsequent to utterance of the deviant spoken input. By way of non-limiting example, the primary spoken input may be related to a first section of a note. The audio information component may be configured to analyze the audio information to determine which individual ones of the spoken inputs are the primary spoken input or the deviant spoken input.

The presentation component may be configured to effectuate presentation of a graphical user interface. The graphical user interface may be presented via the user interface of the client computing platform. The graphical user interface may present sections of the note and/or other information. By way of non-limiting example, the sections of the note may include the first section, a second section, other sections, and/or other information.

The amendment component may be configured to determine which section of the note to which the deviant spoken input is related. The determination may be based on analysis. As such, relatedness of the deviant spoken input to the second section of the note may be determined. The amendment component may be configured to alternately amend sections of the note. Amending the sections of the note may include deviating from one section to another section and returning back to the one section for continued population. As such, the temporal ordering the amendments may mimic the temporal ordering of the spoken inputs. The amending may be based on the determination. By way of non-limiting example, the first section may be amended based on a first portion the primary spoken input, subsequently the second section is amended based on the deviant spoken input, and subsequently the first section is amended based on a second portion of the primary spoken input in accordance with the temporal ordering of the first portion of the primary spoken input, the deviant may be spoken input, and the second portion of the primary spoken input within the audio information.

The presentation component may be configured to effectuate, via the user interface, presentation of the alternating amendments to the sections of the note.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
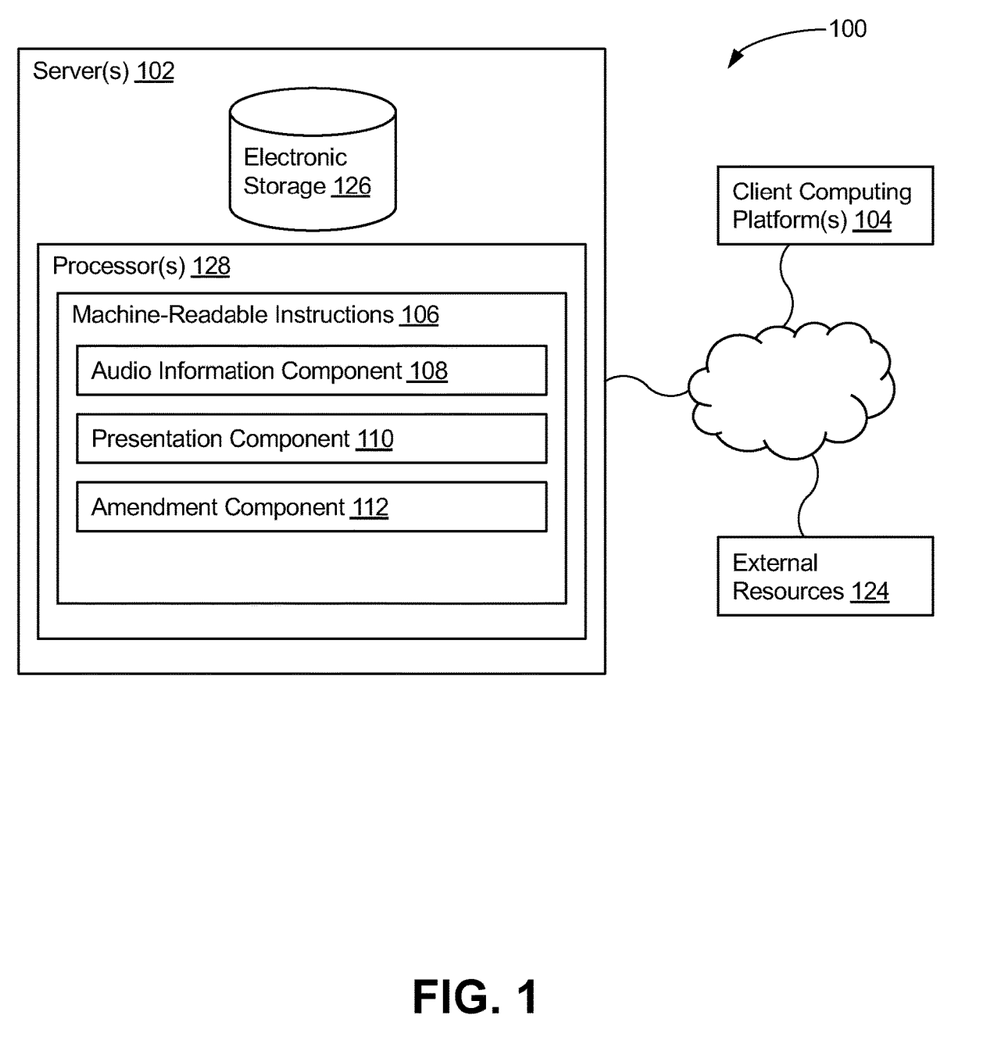
FIG. 1 illustrates a system configured to briefly deviate from and resume back to amending a section of a note, in accordance with one or more implementations.

FIG. 1 illustrates a system 100 configured to briefly deviate from and resume back to amending a section of a note, in accordance with one or more implementations. In some implementations, system 100 may include one or more servers 102. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Client computing platform(s) 104 may include a user interface, an audio section, and/or other components. A given user may provide user input via the user interface, the audio section, and/or the other components of client computing platform(s) 104. The user may be a doctor, healthcare personnel, a scribe, a clerk, a student, and/or other users. The user interface may include, by way of non-limiting example, a touchscreen, keyboard, mouse, trackpad, keypad, stylus, and/or other user interface that may facilitate user input, presentation of information, and/or other functions. The audio section may include an audio input sensor (e.g., a microphone) and/or other audio components.

Server(s) 102 may be configured by machine-readable instructions 106. Machine-readable instructions 106 may include one or more instruction components. The instruction components may include computer program components. The instruction components may include one or more of audio information component 108, presentation component 110, amendment component 112, and/or other instruction components.

Presentation component 110 may be configured to effectuate presentation of a graphical user interface. The graphical user interface may be presented via the user interface of client computing platform 104. The graphical user interface may enable the user to view one or more notes and/or other information. The graphical user interface may present one or more sections of a note and/or other information. The sections of the note may include a first section, a second section, and/or other sections. In some implementations, individual sections may include one or more of a parameter, a parameter value, a section name value, a code, a code value, description, title value, and/or other information. Parameters may specify measurable, recordable, and/or determined information. Parameter values corresponding to the parameters may define a particular value, numerical or non-numerical, that characterizes a subject/focus (e.g., patient) of the note. In some implementations, the note may be stored to electronic storage 126 and/or other storage automatically and/or responsive to manual input.

By way of non-limiting illustration, the parameters may be related to healthcare and characterize a patient who is the focus of the note and/or an appointment of the patient. The parameter values may define a patient name, date of birth, appointment date, healthcare provider (e.g., professional title and name), age, weight, height, blood pressure, heart rate, body temperature, allergies, prescriptions, and/or other parameters. In some implementations, some of the parameters and the corresponding parameter values may be categorized as patient parameters, appointment parameters, healthcare provider parameters, and/or other parameters. It is to be understood that descriptions herein related to healthcare and patients are for illustrative purposes only and are not intended to be limiting as the parameters, the parameter values, and the subject/focus of the note may be utilized in a plurality of contexts other than healthcare.

Figure 4:
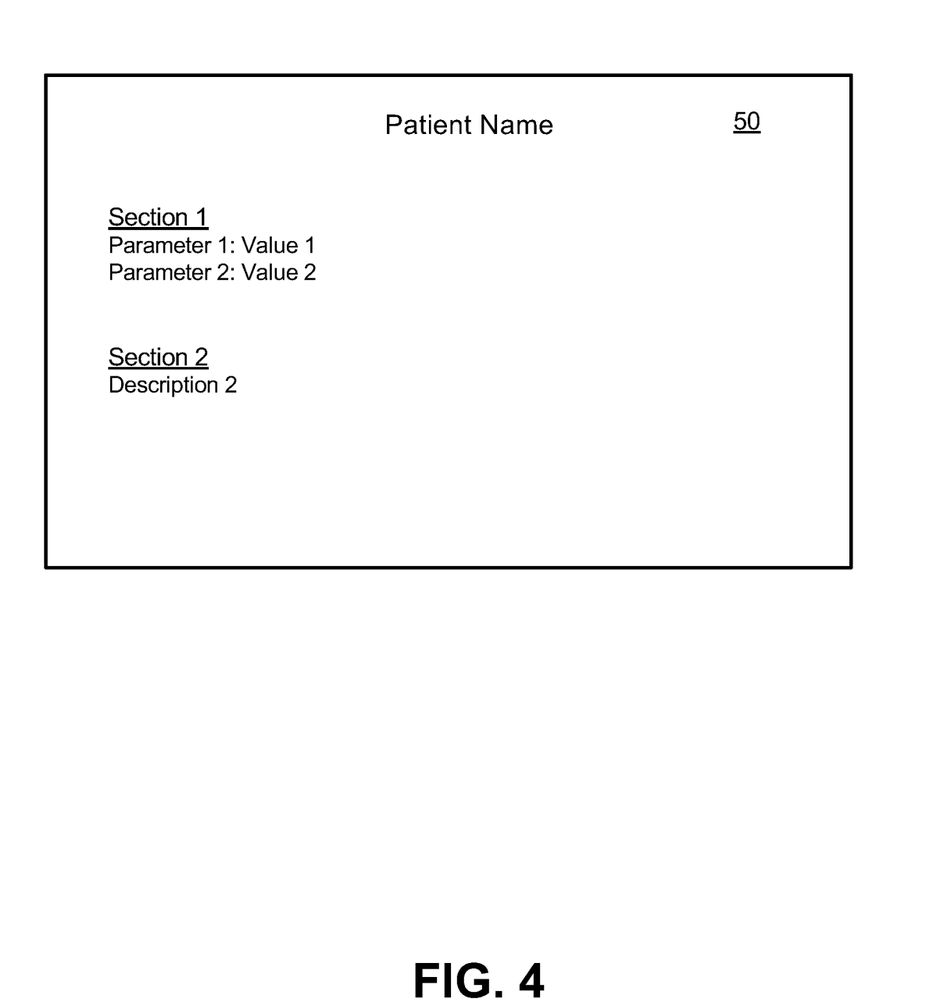
FIG. 4 illustrates an example implementation of the note, in accordance with one or more implementations.

FIG. 4 may illustrate an example implementation of the note, in accordance with one or more implementations. FIG. 4 may include a note format 50. Note format 50 may indicate an overarching nature of a structure of the note described herein. Note format 50 is for illustrative purposes only and is not intended to be limiting of note formats that may be created, amended, and/or saved related to a particular subject (e.g., patient). Note format 50 may include a patient name as a title, a section 1, a section 2, and/or other sections. In some implementations, the title may be defined by one or more other parameter values (e.g., an appointment type). Section 1 may include a parameter 1, a parameter 2, and/or other parameters. Parameter 1 and parameter 2 may correspond to value 1 and value 2, respectively. That is, value 1 defines parameter 1 and value 2 defines parameter 2. Section 2 may define a description 2. Description 2 may include explanations, qualitative analysis, and/or other information regarding the patient.

Referring back to FIG. 1, audio information component 108 may be configured to obtain audio information representing sound captured by the audio section of client computing platform 104. The sound may include speech from a user associated with the client computing platform 104 and/or other users (e.g., the patient). The audio information may include spoken inputs uttered by the user and/or other information. The spoken inputs may include primary spoken input, one or more deviant spoken inputs, and/or other spoken inputs. In some implementations, the spoken inputs may include a word spoken by the user, phrases spoken by the user, and/or other spoken inputs.

The primary spoken input may define information that the user explicitly specified where in the note such information should be or is related to. One or more of the deviant spoken inputs may define information the user uttered within utterance or during utterance of the primary spoken input and is intended to be in or is related to one or more different sections of the note than the primary spoken input. Individual deviant spoken inputs may be related to separate sections, parameters, and/or parts of the note. Thus, portions of the primary spoken input may be spoken temporally prior to and subsequent to utterance of the one or more deviant spoken inputs. By way of non-limiting illustration, the primary spoken input may be related to the first section of the note and the deviant spoken input may be related to a different section of the note (e.g., the second section).

In some implementations, the deviant spoken inputs may be uttered casually or may be uttered as commands. The casual utterance of the deviant spoken inputs may include different information than the information defined by the primary spoken input without a command to perform an action (e.g., update, remove, insert, replace, etc.). The deviant spoken input utter as commands may indicate to amend (i.e., perform an action) the one or more sections of the note. Amendments to the note or the one or more sections thereof may include inserting information (e.g., text, a file, an image, etc.) to the note, deleting information from the note, emphasizing text in the note (e.g., highlighting, bolding, underlining, italicizing, etc.), replacing text in the note, and/or other amendments to the note. By way of non-limiting illustration, a casually uttered deviant spoken input may include "oh, and her heart rate is 120 beats per minute" while a command as the deviant spoken input may include "insert 120 beats per minute as her heart rate".

In some implementations, individual deviant spoken inputs may be uttered by the user consecutively where portions of the primary spoken input are utter temporally prior to and subsequent to the consecutive deviant spoken inputs. In some implementations, the individual deviant spoken inputs may be utter by the user separately (i.e., non-consecutively) wherein portions of the primary spoken input are uttered temporally prior to and/or subsequent to each of the deviant spoken inputs.

In some implementations, particular words and/or phrases included in the spoken inputs may correspond to one of the pre-set words and/or phrases that are relevant to particular commands. For example, a word "enter" may be recognized and correspond to words "insert" and "input" of which are relevant and correspond to a text insertion command and thus correspond to the inserting amendment.

Audio information component 108 may be configured to analyze the audio information to determine which individual ones of the spoken inputs are the primary spoken input or the deviant spoken input. In some implementations, analyzing the audio information may include performing speech recognition on the audio information. Text resulting from the speech recognition may be analyzed to determine which of the individual spoken inputs are the primary spoken input or the deviant spoken input. The speech recognition may be performed by various known speech recognition techniques to determine the text from the spoken inputs and/or other techniques. In some implementations, the performance of speech recognition on the audio information may be performed by one or more processors remote from the client computing platform 104 associated with the user and/or server(s) 102. The audio information may be transmitted over a network to/from the remote one or more processors.

In some implementations, analysis of the text to determine which of the individual spoken inputs are the primary spoken input or the deviant spoken input may be performed by one or more known text analysis systems remote from client computing platform 104 and/or server(s) 102. The text resultant from the speech recognition may be transmitted over the network to/from the one or more text analysis systems. In some implementations, analysis of the text may be performed by audio information component 108. In some implementations, audio information component 108 may be configured to perform known machine learning techniques and/or natural language processing to determine which of the individual spoken inputs are the primary spoken input or the deviant spoken input from the text resultant from the speech recognition.

In some implementations, analyzing the audio information and/or the text from the speech recognition may include identifying trigger words and/or phrases to determine which of the individual spoken inputs are the primary spoken input or the deviant spoken input. The trigger words and/or phrases may include one or more words and/or one or more phrases that are not related to the section that the primary spoken input is related to and/or is more closely related to a different section, parameter, and/or part of the note. For example, when the user dictates "the patient has a swollen right ankle, and her height is five four; she twisted it running" for a Symptoms section, a trigger word spoken by the user may be "height" because her height is not related to her ankle and/or is more related to a Stats section, particularly a height parameter, of the note.

In some implementations, the spoken inputs may include the commands to amend the one or more sections of the note. The commands may be determined from the analysis of the audio information. Amendment component 112 may be configured to interpret the commands from the spoken inputs to determine the amendments to execute for particular sections. In some implementations, interpreting the commands may include determining a parameter value to a parameter. For example, amendment component 112 may interpret the command "insert 120 beats per minute as her heart rate" for a subsequent amendment of a heart rate parameter value to be "120 BPM".

Amendment component 112 may be configured to determine which sections of the note, parameters, and/or other part of the note to which the individual deviant spoken inputs are related. The determination may be based on analysis of the audio information. In some implementations, determining which part of the note the deviant spoken input is related to may include amendment component 112 identifying the trigger words and/or phrases included in the deviant spoken inputs. The trigger words and/or phrases may include one or more of a section name, a parameter, and/or other trigger words and/or phrases. For example, "blood pressure", "blood sugar", and "heart rate" may be parameters that have corresponding values and may be trigger words and/or phrases spoken by the user. As another example, "allergic" may be a trigger word spoken by the user indicating an allergy of a patient and thus related to an Allergies section of the note. As another example, "is taking" or "is currently on" may be trigger words and/or phrases spoken by the user indicating prescriptions of the patient and thus related to a Prescriptions section of the note. By way of non-limiting illustration, relatedness of the deviant spoken input to the second section of the note may be determined.

The words and/or phrases utter by the user, and utterance itself thereof, may have a semantic field similarity. That is, a set of words and/or phrases may relate to the same meaning or refer to the same thing. For example, a first user may pronounce the term "abdomen" differently than a second user, where the second user is different from the first user. As another example, the first user may utter/use the term "diabetes" and the second user may utter the term "sugar level" where "diabetes" and "sugar level" may refer to the same meaning or parameter value.

Amendment component 112 may be configured to alternately amend sections of the note by deviating from one section to another section and returning back to the one section for continued population and/or amending of the note so that the temporal ordering the amendments mimic the temporal ordering of the spoken inputs. The alternating amending may be based on the determination of which individual sections the deviant spoken inputs are related to. The alternating amending may be performed in real time or near-real time. As previously described, the amendments may include inserting or populating information (e.g., text), deleting information, emphasizing information, replacing information, and/or other amendments. As such, multiple sections of the note may be, for example, populated with information while the user intended to populate a particular section of the note.

By way of non-limiting illustration, the first section may be amended based on the first portion the primary spoken input. Subsequently, the second section may be amended based on the deviant spoken input and subsequently, the first section may be amended based on the second portion of the primary spoken input. Such amending may be in accordance with the temporal ordering of the first portion of the primary spoken input, the deviant spoken input, and the second portion of the primary spoken input within the audio information. The first portion and the second portion of the primary spoken input may collectively comprise information for the first section of the note and the deviant spoken input may, itself, comprise information for the second section of the note. In some implementations, amendments of the note may be based on the text resulted from the speech recognition. For example, the spoken inputs may be transcribed into the text for analysis to determine whether they are the primary spoken input or the deviant spoken inputs and further for populating/inserting the text as part of a particular section.

In some implementations, amendment component 112 may be configured to obtain user input indicating where in the note the primary spoken input is related and thus amended in accordance with the primary spoken input. The user input may be in the form of a physical input via the user interface or in the form of spoken inputs obtained via the audio section. The physical input via the user interface may include a screen tap of the touchscreen, a screen drag of a part of the touchscreen, a touch-and-hold of a part of the touchscreen, clicking of the mouse, pressing of one or more virtual buttons, keystrokes of the keyboard, movement of the trackball (e.g., to move a cursor), utilization of the stylus on the touchscreen, and/or other physical input. The user input in the form of a spoken input may include utterance of a particular section, parameter, and/or other portion of the note (e.g., "Suki, Symptoms"). By way of non-limiting illustration, the user input may indicate that the first section of the note is to be amended in accordance with the primary spoken input. As such, in some implementations, a visual indicator may be presented to indicate that the first section will be amended in accordance with the primary spoken input.

Presentation component 110 may be configured to effectuate presentation of the alternating amendments to the sections of the note and/or other information. The presentation may be via the graphical user interface. Thus, the user may view, in real time or near-real time, amendments to the sections of the note based on the primary spoken input and the one or more deviant spoken inputs. By way of non-limiting illustration, the user may view that the first section is being amended in accordance with the primary spoken input (i.e., the first portion) and subsequently the second section is being amended in accordance with the deviant spoken input, and further subsequently the first section may continue being amended in accordance with the primary spoken input (i.e., the second portion). In some implementations, presentation of indicia may visually indicate, to the user, where in the note a particular spoken input has been determined to be related to and thus where amendments may be performed. The indicia may include a change in background color (e.g., highlighting to be darker, highlighting to be a particular color, etc.), icons (e.g., three dots), and/or other indicia to indicate that a particular part of the note will be amended based on the spoken inputs. By way of non-limiting example, while amending a particular section or parameter value (e.g., the second section), such section or corresponding parameter may be more prominent than the rest of the note (e.g., the rest of the note is greyed out). As such, prominence of a section and/or parameter value and its corresponding parameter may alternate according to what is being amended.

Figure 3A:
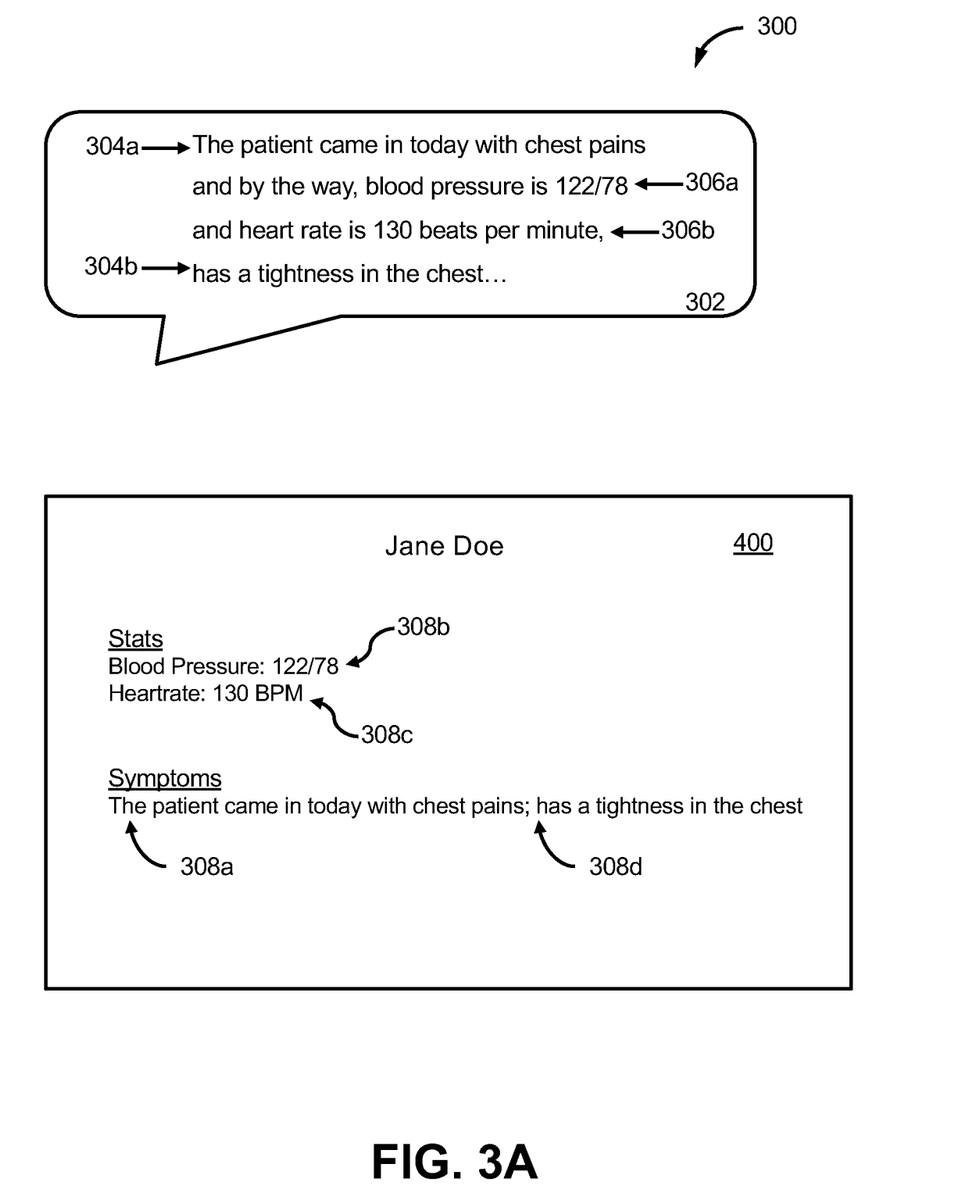
FIG. 3A-B illustrate an example implementation of the system configured to briefly deviate from and resume back to amending a section of a note, in accordance with one or more implementations.

FIG. 3A illustrates an example implementation of the system configured to briefly deviate from and resume back to amending a section of a note, in accordance with one or more implementations. FIG. 3A illustrates example implementation 300. Example implementation 300 may exemplify note format 50 of FIG. 4. Example implementation 300 may include audio information 302 spoken by a user (e.g., a doctor) and a note 400 that may be amended based on the audio information 302. Audio information 302 may include a portion 304a of a primary spoken input, a deviant spoken input 306a, a deviant spoken input 306b, and a portion 304b of the primary spoken input. A section of the note, Symptoms section, may be indicated by the user (e.g., tap to the Symptoms section) to be amended in accordance with the primary spoken input. Thus, amendment 308a may be inserted under Symptoms based on portion 304a. Subsequent to utterance of portion 304a, deviant spoken input 306a and deviant spoken input 306b may be uttered by the user. It may be determined that deviant spoken input 306a and deviant spoken input 306b are related to a Stats section of note 400 (and not Symptoms). Thus, amendment 308b and amendment 308c may be inserted under Stats based on deviant spoken input 306a and deviant spoken input 306b, respectively. Portion 304b may be uttered subsequent to deviant spoken input 306b. Thus, amending of the note may resume back to the Symptoms section and amendment 308d may be inserted based on portion 304b.

Figure 3B:
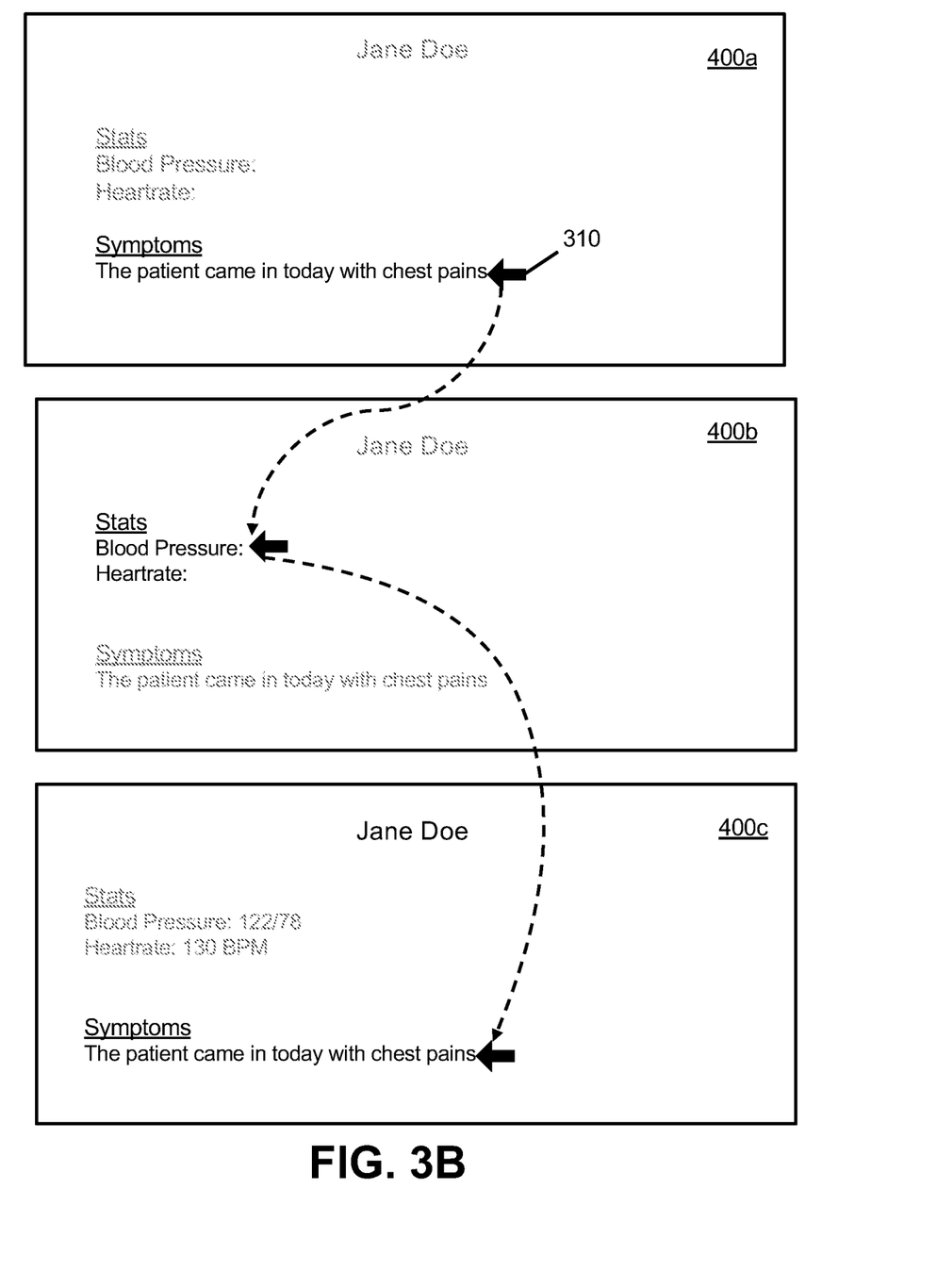

FIG. 3B illustrates an example implementation of the system configured to briefly deviate from and resume back to amending a section of a note, in accordance with one or more implementations. FIG. 3B may illustrate note 400 (as notes 400a-c) of FIG. 3A subsequent to individual amendments that are based on the individual spoken inputs of audio information 302. FIG. 3A may be referred to simultaneously with FIG. 3B. Note 400a may present amendment 308a that is based on portion 304a. The Symptoms section may be more visually prominent than the rest of note 400a and may include indicia 310 as a visual indicator of what part of the note is being amended at a point in time. As illustrated in note 400b, the Stats section may be more visually prominent than the rest of note 400b and indicia 310 may move to under the Stats section based on deviant spoken input 306a and deviant spoken input 306b. As such, amendment 308b may be inserted based on deviant spoken input 306a as illustrated in note 400c. Subsequently, indicia 310 may move to near a heartrate parameter and amendment 308c may be inserted based on deviant spoken input 306b. Based on portion 304b, the Symptoms section may, again, be more visually prominent than the rest of note 400c and indicia 310 may move back to its original location as in note 400a prior to amendments 308b and 308c. As such, amendment 308d may be inserted under the Symptoms section based on portion 304b.

In some implementations, server(s) 102, client computing platform(s) 104, and/or external resources 124 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 124 may be operatively linked via some other communication media.

A given client computing platform 104 may include one or more processors configured to execute computer program components. The computer program components may be configured to enable an expert or user associated with the given client computing platform 104 to interface with system 100 and/or external resources 124, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 124 may include sources of information outside of system 100, external entities participating with system 100, and/or other resources. In some implementations, some or all of the functionality attributed herein to external resources 124 may be provided by resources included in system 100.

Server(s) 102 may include electronic storage 126, one or more processors 128, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 126 may comprise non-transitory storage media that electronically stores information. The electronic storage media of electronic storage 126 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 126 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 126 may include one or more virtual storage resources (e.g., cloud storage, a virtual private network, and/or other virtual storage resources). Electronic storage 126 may store software algorithms, information determined by processor(s) 128, information received from server(s) 102, information received from client computing platform(s) 104, and/or other information that enables server(s) 102 to function as described herein.

Processor(s) 128 may be configured to provide information processing capabilities in server(s) 102. As such, processor(s) 128 may include one or more of a digital processor, an analog processor, a digital circuit designed to process information, an analog circuit designed to process information, a state machine, and/or other mechanisms for electronically processing information. Although processor(s) 128 is shown in FIG. 1 as a single entity, this is for illustrative purposes only. In some implementations, processor(s) 128 may include a plurality of processing units. These processing units may be physically located within the same device, or processor(s) 128 may represent processing functionality of a plurality of devices operating in coordination. Processor(s) 128 may be configured to execute components 108, 110, and/or 112, and/or other components. Processor(s) 128 may be configured to execute components 108, 110, and/or 112, and/or other components by software; hardware; firmware; some combination of software, hardware, and/or firmware; and/or other mechanisms for configuring processing capabilities on processor(s) 128. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, and/or 112 are illustrated in FIG. 1 as being implemented within a single processing unit, in implementations in which processor(s) 128 includes multiple processing units, one or more of components 108, 110, and/or 112 may be implemented remotely from the other components. The description of the functionality provided by the different components 108, 110, and/or 112 described below is for illustrative purposes, and is not intended to be limiting, as any of components 108, 110, and/or 112 may provide more or less functionality than is described. For example, one or more of components 108, 110, and/or 112 may be eliminated, and some or all of its functionality may be provided by other ones of components 108, 110, and/or 112. As another example, processor(s) 128 may be configured to execute one or more additional components that may perform some or all of the functionality attributed below to one of components 108, 110, and/or 112.

Figure 2:
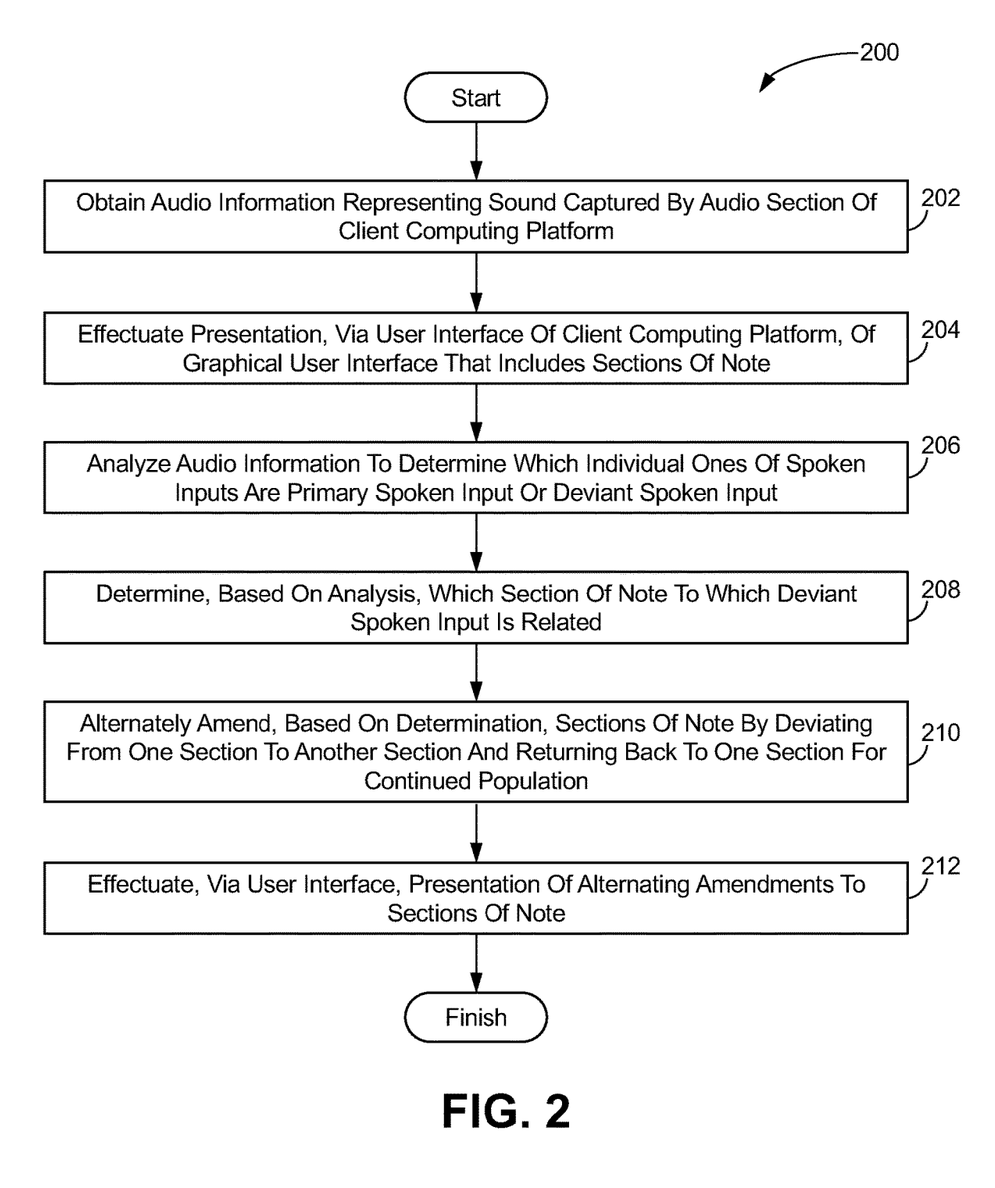
FIG. 2 illustrates a method to briefly deviate from and resume back to amending a section of a note, in accordance with one or more implementations.

FIG. 2 illustrates a method 200 to briefly deviate from and resume back to amending a section of a note, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include obtaining audio information representing sound captured by an audio section of a client computing platform. The sound may include speech from a user associated with the client computing platform. The audio information may include spoken inputs uttered by the user. The spoken inputs may include primary spoken input and deviant spoken input. Portions of the primary spoken input may be spoken temporally prior to and subsequent to utterance of the deviant spoken input. The primary spoken input may be related to a first section of a note. Operation 202 may be performed by one or more hardware processors configured by machine-readable instructions including a component that is the same as or similar to audio information component 108, in accordance with one or more implementations.

An operation 204 may include effectuating presentation, via the user interface of the client computing platform, of a graphical user interface that includes sections of the note. Operation 204 may be performed by one or more hardware processors configured by machine-readable instructions including a component that is the same as or similar to presentation component 110, in accordance with one or more implementations.

An operation 206 may include analyzing the audio information to determine which individual ones of the spoken inputs are the primary spoken input or the deviant spoken input. Operation 206 may be performed by one or more hardware processors configured by machine-readable instructions including a component that is the same as or similar to audio information component 108, in accordance with one or more implementations.

An operation 208 may include determining, based on analysis, which section of the note to which the deviant spoken input is related. Operation 208 may be performed by one or more hardware processors configured by machine-readable instructions including a component that is the same as or similar to amendment component 112, in accordance with one or more implementations.

An operation 210 may include alternately amending, based on the determination, sections of the note by deviating from one section to another section and returning back to the one section for continued population. As such, the temporal ordering the amendments mimic the temporal ordering of the spoken inputs. Operation 210 may be performed by one or more hardware processors configured by machine-readable instructions including a component that is the same as or similar to amendment component 112, in accordance with one or more implementations.

An operation 212 may include effectuating, via the user interface, presentation of the alternating amendments to the sections of the note. Operation 212 may be performed by one or more hardware processors configured by machine-readable instructions including a component that is the same as or similar to presentation component 110, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to briefly deviate from and resume back to amending a section of a note, the system comprising:
   one or more processors configured by machine-readable instructions to:
      obtain audio information that includes spoken inputs uttered by a user via a client computing platform, the spoken inputs including primary spoken input and deviant spoken input, wherein portions of the primary spoken input are spoken temporally prior to and subsequent to utterance of the deviant spoken input, wherein the primary spoken input is related to a particular section of a note, wherein the spoken inputs include utterances of commands that include predefined phrases and utterances that are casually uttered without the predefined phrases;
      analyze the audio information to determine which individual ones of the spoken inputs are the primary spoken input or the deviant spoken input, wherein analyzing the audio information includes identifying trigger words and/or phrases that are related to other sections of the note that are not the particular section of the note;
      determine, based on analysis, which section of the note to which the deviant spoken input is related; and
      alternately amend, based on the determination, sections of the note by deviating from one section to another section and returning back to the one section for continued population so that the temporal ordering of the amendments mimics the temporal ordering of the spoken inputs.

2. The system of claim 1, wherein analyzing the audio information includes performing speech recognition on the audio information to facilitate determining which of the individual spoken inputs are the primary spoken input or the deviant spoken input.

3. The system of claim 1, wherein the commands include commands to amend the sections of the note.

4. The system of claim 3, wherein the one or more processors are further configured by the machine-readable instructions to:
   interpret the commands from the spoken inputs to determine the amendments to execute for particular sections.

5. The system of claim 4, wherein the amendments include inserting text, deleting text, emphasizing text, and/or replacing text.

6. The system of claim 1, wherein the one or more processors are further configured by the machine-readable instruction to:
   obtain user input that the particular section of the note is to be amended in accordance with the primary spoken input.

7. The system of claim 6, wherein the user input is in the form of a physical input via a user interface or in the form of spoken inputs obtained via the audio section.

8. The system of claim 1, wherein the spoken inputs include phrases spoken by the user.

9. A method to briefly deviate from and resume back to amending a section of a note, the method comprising:
   obtaining audio information that includes spoken inputs uttered by a user via a client computing platform, the spoken inputs including primary spoken input and deviant spoken input, wherein portions of the primary spoken input are spoken temporally prior to and subsequent to utterance of the deviant spoken input, wherein the primary spoken input is related to a particular section of a note, wherein the spoken inputs include utterances of commands that include predefined phrases and utterances that are casually uttered without the predefined phrases;
   analyzing the audio information to determine which individual ones of the spoken inputs are the primary spoken input or the deviant spoken input, wherein analyzing the audio information includes identifying trigger words and/or phrases that are related to other sections of the note that are not the particular section of the note;
   determining, based on analysis, which section of the note to which the deviant spoken input is related; and
   alternately amending, based on the determination, sections of the note by deviating from one section to another section and returning back to the one section for continued population so that the temporal ordering of the amendments mimics the temporal ordering of the spoken inputs.

10. The method of claim 9, wherein analyzing the audio information includes performing speech recognition on the audio information to facilitate determining which of the individual spoken inputs are the primary spoken input or the deviant spoken input.

11. The method of claim 9, wherein the commands include commands to amend the sections of the note.

12. The method of claim 11, further comprising:
interpreting the commands from the spoken inputs to determine the amendments to execute for particular sections.

13. The method of claim 12, wherein the amendments include inserting text, deleting text, emphasizing text, and/or replacing text.

14. The method of claim 9, further comprising:
obtaining user input that the particular section of the note is to be amended in accordance with the primary spoken input.

15. The method of claim 14, wherein the user input is in the form of a physical input via a user interface or in the form of spoken inputs obtained via the audio section.

16. The method of claim 9, wherein the spoken inputs include phrases spoken by the user.

\* \* \* \* \*